United States Patent
Fujishima

[11] Patent Number: 5,884,630
[45] Date of Patent: Mar. 23, 1999

[54] METHOD FOR DIAGNOSING DRY EYES

[75] Inventor: Hiroshi Fujishima, Ichikawa, Japan

[73] Assignee: Taisho Pharmaceutical Co., Ltd., Tokyo, Japan

[21] Appl. No.: 773,520

[22] Filed: Dec. 23, 1996

[30] Foreign Application Priority Data

Dec. 28, 1995 [JP] Japan ................................ 7-343227

[51] Int. Cl.$^6$ .............................................. A61B 19/00
[52] U.S. Cl. ........................................... 128/898; 600/318
[58] Field of Search ............................ 128/898; 600/307, 600/549, 310, 318, 473, 474, 300

[56] References Cited

U.S. PATENT DOCUMENTS

| | | | |
|---|---|---|---|
| 4,461,303 | 7/1984 | Refojo et al. | 600/307 |
| 5,115,815 | 5/1992 | Hansen | 600/474 |
| 5,143,080 | 9/1992 | York | 600/549 |
| 5,348,551 | 9/1994 | Spears et al. | 606/5 |

*Primary Examiner*—Mickey Yu
*Assistant Examiner*—Kelly O'Hara
*Attorney, Agent, or Firm*—Sughrue, Mion, Zinn, Macpeak & Seas, PLLC

[57] ABSTRACT

Dry eyes are more objectively and exactly diagnosed on the basis a rate of decrease in corneal surface temperature due to the heat vaporization in tear evaporation as determined by measuring corneal surface temperatures in time course from one blinking to next blinking of eyes of patients by an infrared radiation thermometry.

6 Claims, 2 Drawing Sheets

CHANGE IN CORNED SURFACE TEMPERATURE AFTER BLINKING

CHANGE IN CORNED SURFACE
TEMPERATURE AFTER BLINKING

METHOD FOR DIAGNOSING DRY EYES

BACKGROUND OF THE INVENTION

1) Field of the Invention

The present invention relates to a method for diagnosing dry eyes, and more particularly to a method for diagnosing dry eyes by measuring corneal surface temperatures after one blinking and determining a rate of decrease in the corneal surface temperature due to the heat of vaporization in the tear evaporation of eyes of patients.

2) Related Art Statement

Dry eyes are a disease occurring as a disorder on the ocular surface, i.e. cornea and conjunctiva surfaces, due to qualitative or quantitative abnormality of tears. With the advent of the current information age office automation is now in rapid progress and consequently the video display terminal work is rapidly growing, resulting in increase in asthenopia or dry eye-complaining patients. It is said that Japan only has a latent dry eye patient population of eight millions. A primary cause of dry eyes has not been clarified yet, but the up-to-date knowledge suggests that the dry eyes are closely related to an abnormal autoimmunity or viruses.

Heretofore, diagnosis of dry eyes has been carried out not by a single test procedure, but by a combination of various test procedures. A particularly important test procedure for the diagnosis is an inquiry and most of asthonopia-complaining patients are diagnosed as suffering from dry eyes. Besides the inquiry, vital staining test and quantative determination of tears have been regarded as essential test procedures. In addition, other test procedures, such as quantitative determination of tear evaporation, have been also in practice.

The vital staining test is carried out by instilling a drop of physiological salt solution of rose bengal or fluoresecein into an eye as a reagent to observe the resulting staining state and measure a tear break-up time (BUT) at the same time [Toda et al: Atarashii Ganka (New Ophthalmology), 8 (7), 1021–1027 (1991)]. The procedure for quantative determination of tears includes a Shirmer's test and a cotton thread test According to the Shirmer's test, a strip of filter paper is attached to a lower eyelid to measure an tear adsorbed distance on the strip to determine a quantity of tears [Goren, M. B. et al: Am. J. Ophtalmol., 106, 570–4 (1988)]. According to the cotton thread test, a cotton thread stained with a pH indicator, etc. in advance is put in contact with tears in an eye and the discolored distance of the thread by tears adsorption is measured to determine an amount of tears [Kunihashi, K. et al; Journal of Ped. Ophthalmol., 14, 390–7 (1977)]. The procedure of determination of tear evaporation includes a method of fixing humidity and temperature microsensors to a chamber, and putting the chamber over to measure a humidity increase within the chamber [Tsubota, K. et al: Invest. Ophtalmol. Vis. sa: 33 (10) 2942–50 (1992)].

Among the above-mentioned conventional test procedures for diagnosing dry eyes, the vital staining test is complicated in operation; the Shirmor's test gives rise to physical pains due to contact of a ship of filter paper with the lower eyelid; the cotton thread test is difficult in test manipulation due to the thinness of thread and consequent easy bending; and the conventional test procedure for quantitative determination of tear evaporation needs expensive apparatuses, etc.

SUMMARY OF THE INVENTION

An object of the present invention is to provide a simple; low cost non-invasive method for diagnosing dry eyes without any pains to eyes.

The present inventor found that temperature always tend to decrease on a vital mucous membrane surface such as an ocular surface always wetted with moistures such as tears, etc., due to the heat of vaporization, where the temperature decrease due to the heat of vaporization is more considerable with increasing water wettability and thus the vital tear wettability of eyes in other words, the vital tear dryness, can be determined by analyzing changes in the ocular surface temperature.

The present inventor further found that the ocular surface temperature starts to decrease just from one blinking due to the heat of vaporization in the tear evaporation from the ocular surface, and the quantity of evaporated tears increase so long as there is a sufficient quantity of tears on the ocular surface, resulting in abrupt decrease in the ocular surface temperature and in case of dry eyes, on the other hand, the quantity of evaporated tear decreases, resulting in gentle decrease in the ocular surface temperature.

As a result of further extensive studies on the basis of these findings, the present inventor has conceived that the tear wettability of ocular surface determined by analyzing changes in ocular surface temperature after one blinking can serve as a significant indicator for diagnozing dry eyes, the present invention is based on this new conception.

Thus the present invention provides a method for diagnosing dry eyes of mammals including human beings, which comprises measuring corneal surface temperatures of mammals including human beings in time course from one blinking to next blinking and determining a rate of decrease in corneal surface temperature due to the heat of vaporization in tear evaporation.

DETAILED DESCRIPTION F THE INVENTION

Figure 1:
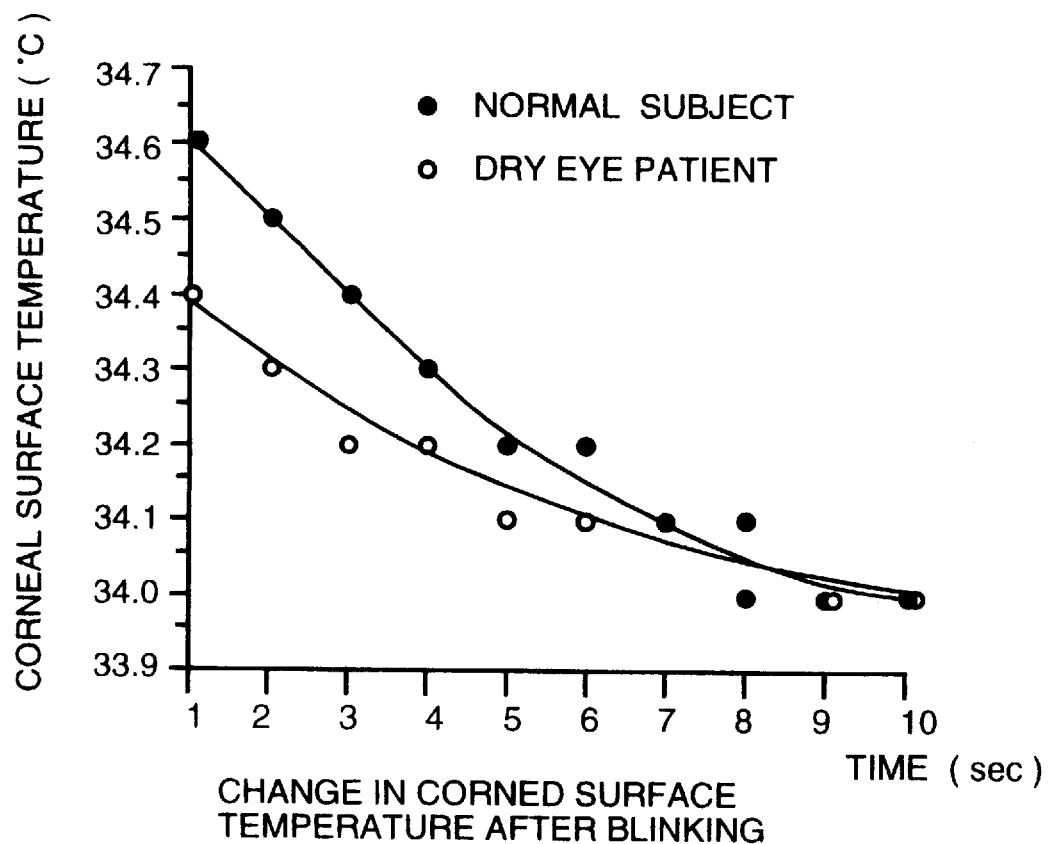
FIG. 1 is a graph showing changes in corneal surface temperature, as measures in the time course from one blinking to next blinking.

According to the present method for diagnosing dry eyes, a corneal surface temperatures are measured in time course from one blinking to next blinking by an infrared radiation thermometry, particularly by a recently developed, high speed, high resolution thermography, such as an infrared radiation thermometer, Model THI-500 (made by Tasko K.K. Osaka, Japan) having an easy-to-handle size such as 14 cm long, 6 cm wide and 7 cm high and only 265 g in weight, which can measure temperatures rouging from 0° C. to 30° C. within about 0.7 seconds with a precision of 0.1° C. Other infrared radiation thermometers having similar functions to those of Model THI-500 can be likewise used in the present invention.

It is preferable to measure corneal surface temperatures by an infrared radiation thermometer placed at a distance of about 30 cm to about 50 cm from the center of the cornea. Actual measurement is preferably carried out in a room kept at a constant temperature of about 25° C. and a constant relative humidity of about 40%.

In the present invention, the corneal surface temperatures are measured in the time course from one blinking to next blinking. Dry eyes are diagnosed on the basis of a rate of decrease in the corneal surface temperature derived from the measured corneal surface temperatures in time course. Eyes with a significantly lower rate of decrease in the corneal surface temperature than that of normal eyes can be diagnosed as dry eyes.

More specifically in the present invention an initial corneal surface temperature $T_0$ just after one blinking and an equilibrium corneal surface temperature $T_\infty$, which is a temperature at an equilibrium just before next blinking after the final gentle decrease in corneal surface temperature, are measured to derive a $(T_0-T_\infty)$ value. Dry eyes are diagnosed on the basis of the $(T_0-T_\infty)$ value thus obtained. That is, eyes whose $(T_0-T_\infty)$ value is smaller than that of normal eyes can be diagnosed as dry eyes. In Example which follows, 10 dry eye patients with an average eye of 53.4 years old had $(T_0-T_\infty)$ values of 0.21±0.8 (°C.), whereas 10 normal subjects with an average age of 33.8 years old had $(T_0-T_\infty)$ values of 0.6±0.28 (°C.). It can be seen from those facts that eyes having a significantly less $(T_0-T_\infty)$ value than that of normal eyes can be diagnosed as dry eyes.

Furthermore, in the present invention, dry eyes can be more objectively diagnosed according to the following specific method:

As described above, an initial corneal surface temperature $T_0$ just after one blinking, i.e. at zero second, and an equilibrium corneal surface temperature $T_\infty$ at an equilibrium just before next blinking are measured. Furthermore, corneal surface temperatures are also measured at predetermined time intervals in the time course from one blinking to next blinking to determine a corneal surface temperatures T at t seconds from one blinking.

Then, $(T_0-T_\infty)$ values are plotted on the axis Y in a graph against time t in seconds on the axis X, from which the following equation is to be derived to obtain a temperature coefficient K:

$$T=(T_0-T_\infty)e^{Kt}+T_\infty$$

The temperature coefficient K shows a rate of decrease in corneal surface temperature, and dry eyes can be more objectively diagnosed on the basis of temperature coefficient K. That is, eyes having a significantly lower temperature coefficient K than that of normal eyes can be diagnosed as dry eyes. The above-mentioned 10 dry eye patients with an average age of 53.4 years old had a temperature coefficient K of 0.1±0.08/sec, whereas the 10 normal subjects with an average age of 33.8 years old had a temperature coefficient K of 0.29±0.16/sec. It can be also seen from these facts that dry eyes can be diagnosed by temperature coefficient K. In the present invention dry eyes can be more exactly diagnosed by a combination of both above-mentioned $(T_0-T_\infty)$ value and temperature coefficient K.

PREFERRED EMBODIMENTS OF THE INVENTION

The present invention will be explained in detail below, referring to Example.

EXAMPLE (1) Diagnosis of dry eyes according to conventional test procedures:
i) A 56 years-old, dry eye-doubtful woman and a normal 33 years-old woman were tested for diagnosis of dry eyes according to the conventional test procedures.

According to the vital staining test [Toda et al: Atarashii Ganka (New Ophthalmology), 8(7), 1021–1027 (1991)], a drop each of sterile preparations containing 1% rose bengal and 1% fluorescein in physiological salt solutions, respectively, were instilled into eyes as reagents to observe the resulting staining state and measure a tear break-up time (BUT). In case of rose bengal staining test, the cornea and conjunctiva were divided into three regions, i.e. ear-side conjunctiva, cornea and nose-side conjunctiva and the staining degree of the individual three region by rose bengal was evaluated as a score, i.e. zero point for no staining, one point for light staining, 2 points for medium staining and 3 points for heavy staining, where a score of total 9 points throughout all the three regions was made a perfect score in the rose bengal staining test, whereas in case of fluorescein staining test the staining degree of only the cornea by fluorescein was likewise evaluated as a score, where a score of 3 points was made a perfect score in the fluoresecein staining test. In the rose bengal staining test a score of 3 points or over (3+) was considered positive, whereas in the fluorescein staining test a score of one point or move (1+) was considered positive. In the BUT test, a BUT value of less than 5 seconds was considered positive.

According to the Shirmer's test [Hamano, T. et al: Folia Ophthalmol. Jpn., 42, 719–27 (1991)], a quantative determination of tears was conducted by instilling a drop of physiological salt solution containing 0.5% fluorescein and 0.4% oxybuprocaine hydrochloride into eyes and measuring a quantity of tears as absorbed on Shirmor's paper, 5 minutes thereafter. A case of a wetted distance on the Shirmer's paper being less than 5 mm was considered positive. Clearance of tears was designated by a fluorescein-stained distance on the Shirmer's paper and evaluated as scores, i.e. 1×, 2×, 4×any 8×. A score of 4× or less was considered positive.

Simultaneously, quantitative determination of tears according to the cotton thread test [Kunihashi, K et al: Journal of Ped. Ophthalmol., 14 , 390–7 (1977)] was also conducted.

A rate of tear evaporation was determined by measuring a rate of water evaporation per eye in the circumstance at a relative humidity of 40% in terms of TEVOS 40 $g/cm^2$ [Tsubota, K et al: Invent. Ophthalmol. Vis. Sa., 33 (10), 2942–50 (1992)]

ii) Results of determinations are shown in Table 1 for the dry eye-doubtful patient and in Table 2 for the normal subject.

TABLE 1

| Dry eye-doubtful female patient (56 years old) | | |
| --- | --- | --- |
| Test procedure | Right eye | Left eye |
| Rose bengal staining | 2+, 2+, 2+ | 2+, 2+, 2+ |
| Fluorescein staining | 3+ | 3+ |
| BUT | 3 sec | 3 sec |
| Cotton thread test | 13 mm | 11 mm |
| Shirmer's test | 2 mm | 2 mm |
| Clearance | 4× | 4× |
| TEVOS40 | 5.15 × $10^7$ $g/cm^2$ | 4.92 × $10^7$ $g/cm^2$ |

TABLE 2

| Normal female subject (33 years old) | | |
| --- | --- | --- |
| Rose bengal staining | 0, 0, 0 | 0, 0, 0 |
| Fluorescein staining | 0 | 0 |
| BUT 11 sec | 11 sec | 11 sec |
| Cotton thread test | 14 mm | 20 mm |
| Shirmer's test | 6 mm | 7 mm |

TABLE 2-continued

| Normal female subject (33 years old) | | |
|---|---|---|
| Clearance | 16× | 16× |
| TEVOS40 | 12.43 × 10⁷ g/cm² | 12.65 × 10⁷ g/cm² |

(2) Diagnosis of dry eyes according to the present invention:

i) 10 patients (average age of 53.4±13.3 years old) having a subjective symptom of dry eyes, who were diagnosed as positive according to at least one of the above-mentioned conventional test procedures only excluding those determined to be 5 mm or more according to the Shirmer's test and 10 normal subjects (average age of 33.8±13.3 years old) having no subjective symptom of dry eyes, who were diagnosed as not positive according to all the above-mentioned conventional test procedures, were tested for diagnosis of dry eyes according to the present invention.

ii) The diagnosis was conducted in a coom at a constant temperature of 25°±1° C. and a constant relative humidity of 40±5%.

Figure 2:
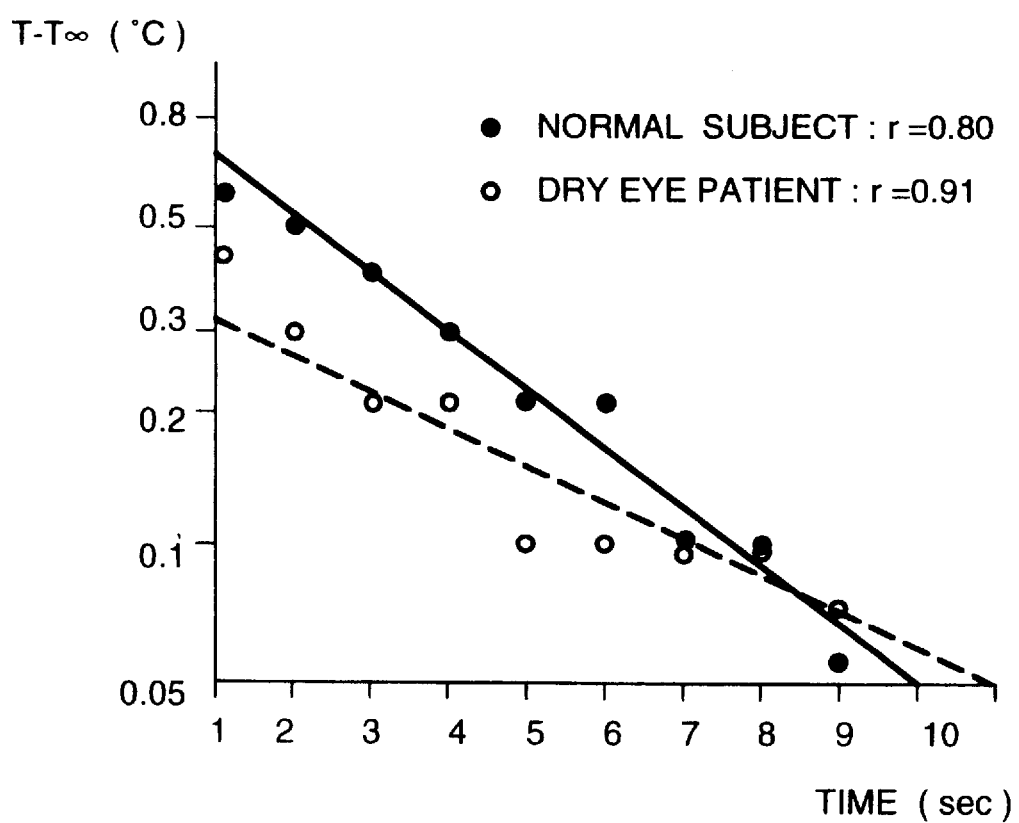
FIG. 2 is a graph showing corneal surface temperatures T in time course t in seconds from one blinking to next blinking by plotting $(T-T_\infty)$ values on the axis Y and time t in seconds on the axis X, where $T_\infty$ is an equilibrium corneal surface temperature, i.e. corneal surface temperature at an equilibrium just before the next blinking.

After having been kept at rest for 15 minutes under normal blinking, the patients and the normal subjects were tested to measure corneal surface temperature T at the center of cornea at every one second for a duration of 10 seconds after one blinking including an initial corneal surface temperature T0 just after the blinking, i.e. at zero second by an infrared radiation thermometer Model THI-500, made by Tasko K.K., Osaka, Japan. That is, an initial corneal surface temperature $T_0$ at zero second just after one blinking and corneal surface temperatures T at every one second after the blinking were measured, where the corneal surface temperature after 10 seconds from the blinking was made an equalibrium corneal surface temperature $T_\infty$.

iii) Changes in corneal surface temperature in the time course just after one blinking are shown in FIG. 1. It can be seen from FIG. 1 that the dry eye patients had a smaller rate of decrease in corneal surface temperature than that of normal subjects.

iv) A graph showing corneal surface temperatures T after t seconds from one blinking to the next blinking by plotting $(T-T_\infty)$ values on the axis Y and time t in seconds on the axis X is given in FIG. 2. The following equation was derived from FIG. 2 to obtain a temperature coefficient K:

$$T=(T_0-T_\infty)e^{kt}+T_\infty$$

Data on the temperature coefficient K, etc. are summarized in Tables 3 and 4, where Table 3 shows the data on dry eye patients and Table 4 shows those on normal subjects. The data were analyzed by t-test.

TABLE 3

| Data on dry eye patients | | | | | | | |
|---|---|---|---|---|---|---|---|
| Tested patient identification | Age (years) | Sex | $T_0$ | $T_\infty$ | $T_0 - T_\infty$ | K | r |
| 1 | 48 | F | 34.4 | 34.1 | 0.3 | 0.21 | −0.89 |
| 2 | 26 | M | 34.1 | 33.9 | 0.2 | 0.21 | −0.77 |
| 3 | 76 | F | 33.6 | 33.3 | 0.2 | 0.14 | −0.71 |
| 4 | 48 | F | 34.3 | 34.2 | 0.1 | 0.07 | −0.77 |
| 5 | 66 | F | 32.7 | 32.6 | 0.1 | 0.07 | −0.77 |
| 6 | 43 | F | 34.6 | 34.4 | 0.2 | 0.21 | −0.77 |
| 7 | 54 | F | 34.4 | 34.1 | 0.3 | 0.29 | −0.89 |
| 8 | 53 | M | 34.1 | 33.9 | 0.2 | 0.14 | −0.71 |
| 9 | 54 | F | 34.6 | 34.3 | 0.3 | 0.07 | −0.88 |

TABLE 3-continued

| Data on dry eye patients | | | | | | | |
|---|---|---|---|---|---|---|---|
| Tested patient identification | Age (years) | Sex | $T_0$ | $T_\infty$ | $T_0 - T_\infty$ | K | r |
| 10 | 66 | F | 33.9 | 33.7 | 0.2 | 0.10 | −0.85 |
| Average age | 53.4 | | 34.1 | 33.9 | 0.21 | 0.15 | −0.80 |

TABLE 4

| Data on normal subjects | | | | | | | |
|---|---|---|---|---|---|---|---|
| Tested patient identification | Age (years) | Sex | $T_0$ | $T_\infty$ | $T_0 - T_\infty$ | K | r |
| 1 | 24 | M | 34.1 | 33.7 | 0.4 | 0.69 | −0.99 |
| 2 | 52 | F | 34.3 | 33.4 | 0.9 | 0.27 | −0.98 |
| 3 | 27 | M | 33.9 | 33.5 | 0.4 | 0.23 | −0.86 |
| 4 | 28 | F | 34.2 | 33.5 | 0.7 | 0.35 | −0.94 |
| 5 | 25 | M | 34.8 | 33.7 | 1.1 | 0.38 | −0.95 |
| 6 | 60 | F | 34.2 | 34.7 | 0.5 | 0.17 | −0.84 |
| 7 | 32 | M | 33.8 | 32.9 | 0.9 | 0.27 | −0.98 |
| 8 | 23 | M | 35.3 | 35.0 | 0.3 | 0.22 | −0.82 |
| 9 | 48 | M | 33.9 | 33.6 | 0.3 | 0.22 | −0.88 |
| 10 | 24 | F | 34.4 | 33.9 | 0.5 | 0.13 | −0.87 |
| Average age | 33.8 | | 34.3 | 33.8 | 0.6 | 0.29 | −0.91 |

It can be seen from Tables 3 and 4 that the dry eye patients had a $(T_0-T_\infty)$ value of 0.2°±0.08° C., whereas the normal subjects had that of 0.6°±0.28° C., showing that the $(T_0-T_\infty)$ value of the dry eye patients were significantly less than that of the normal subjects (P<0.05); the dry eye patients had a correlation factor r of 0.80±0.07, whereas the normal subjects had an r value of 0.91±0.06, showing good correlations there between; and the dry eye patients had a temperature coefficient K of 0.15±0.08/sec, whereas the normal subjects had a K value of 0.29±0.16/sec, showing that the K value of the dry eye patients is significantly less than that of the normal subject.

As explained in detail above, dry eyes can be more objectively and exactly diagnosed in the present invention on the basis of a rate of decrease in corneal surface temperature by measuring corneal surface temperatures in the time course from one blinking to the next to determine the rate of decrease in the corneal surface temperature due to the rate of vaporization in the tear evaporation. That is, the present invention provides a simple, low cost, highly significant method for diagnosing dry eyes more exactly.

What is claimed is:

1. A method for diagnosing dry eyes of a mammal including a human being, which comprises measuring corneal surface temperatures of an ocular surface of said mammal versus time from one blinking to a next blinking, and determining a rate of decrease of the corneal surface temperature due to heat of vaporization via evaporation.

2. A method according to claim 1, wherein the corneal surface temperatures are measured by an infrared radiation thermometry.

3. A method according to claim 1 or 2, further comprising comparing a rate of decrease in the corneal surface temperature of said mammal being diagnosed to a rate of decrease in the corneal surface temperature of a normal mammal.

4. A method according to claim 1 wherein dry eyes are diagnosed on the basis of a $(T_0-T_\infty)$ value as determined by measuring an initial corneal surface temperature $T_0$, and an equilibrium corneal surface temperature $T_\infty$ at an equilibrium just before next blinking.

5. A method according to claim 1 wherein dry eyes are diagnosed on the basis of a temperature factor K determined by the following equation:

$$T=(T_0-T_\infty)e^{Kt}+T_\infty$$

by measuring an initial corneal surface temperature $T_0$ in time course t in seconds from the blinking, and an equilibrium surface temperature $T_\infty$ at an equilibrium just before next blinking and plotting $(T-T_\infty)$ values against time t.

6. A method according to claim 4 or 5, further comprising comparing $(T_0-T_\infty)$ values and temperature coefficient K of said mammal being diagnosed to the $(T_0-T_\infty)$ values and temperature coefficient K of a normal mammal.

* * * * *

UNITED STATES PATENT AND TRADEMARK OFFICE
CERTIFICATE OF CORRECTION

PATENT NO.: 5,884,630
DATED: March 23, 1999
INVENTOR(S): Fujishima et al.

It is certified that error appears in the above-indentified patent and that said Letters Patent is hereby corrected as shown below:

```
On the title page, under item [19], insert --et al.--, after
"Fujishima"; and
```

Item 75, Title page should be as follows:
  --[75] Inventor: Hiroshi Fujishima, Ichikawa, Japan
                 Kazuo Tsubota, Funabashi, Japan --

Signed and Sealed this

Twenty-eighth Day of September, 1999

Attest:

Q. TODD DICKINSON

*Attesting Officer*      *Acting Commissioner of Patents and Trademarks*